(12) United States Patent
DeRiso, II et al.

(10) Patent No.: US 10,959,874 B2
(45) Date of Patent: Mar. 30, 2021

(54) AMELIORATION OF SLEEP APNEA AND OTHER OBSTRUCTIVE BREATHING DISORDERS

(71) Applicants: Anthony J. DeRiso, II, Sandusky, OH (US); Albert N. Santilli, Pepper Pike, OH (US)

(72) Inventors: Anthony J. DeRiso, II, Sandusky, OH (US); Albert N. Santilli, Pepper Pike, OH (US)

( * ) Notice: Subject to any disclaimer, the term of this patent is extended or adjusted under 35 U.S.C. 154(b) by 387 days.

(21) Appl. No.: 16/034,062

(22) Filed: Jul. 12, 2018

(65) Prior Publication Data

US 2018/0338855 A1 Nov. 29, 2018

Related U.S. Application Data

(63) Continuation-in-part of application No. 14/471,849, filed on Aug. 28, 2014, now Pat. No. 10,098,780, which is a continuation-in-part of application No. 13/594,625, filed on Aug. 24, 2012, now Pat. No. 9,775,739.

(Continued)

(51) Int. Cl.
    *A61F 5/56* (2006.01)
    *A61F 5/37* (2006.01)
    *A61F 5/055* (2006.01)

(52) U.S. Cl.
    CPC .............. *A61F 5/56* (2013.01); *A61F 5/3707* (2013.01); *A61F 5/055* (2013.01)

(58) Field of Classification Search
    CPC ...... A61F 5/56; A61F 2005/563; A61F 5/566; A61F 5/58; A61F 5/055; A61F 5/3707; A61F 5/05883; A61F 5/05833; A61F 5/05816; A61F 5/05; A61F 5/042; A61F 5/048; A61F 2007/0009; A61F 2007/0011;

(Continued)

(56) References Cited

U.S. PATENT DOCUMENTS 1,587,558 A * 6/1926 Sheffield ................ A45D 44/22
                                                                                            128/848
4,901,737 A     2/1990   Toone
(Continued)

OTHER PUBLICATIONS

ITA-MED Co., 25377 Huntwood Avenue, Hayward, CA 94544, model No. CC-260, http://www.itamed.com/our-products/back-neck-supports/cervical-collars/ita-med-rigid-plastic-cervical-collar-i-cc-260.html.

(Continued)

*Primary Examiner* — Tarla R Patel
(74) *Attorney, Agent, or Firm* — Wayne D. Porter, Jr.

(57) ABSTRACT

A method and apparatus for the amelioration of sleep apnea and other obstructive breathing disorders in a patient includes a collar configured to encircle the patient's neck, and a jaw-engagement mechanism carried by the collar. The jaw-engagement mechanism includes a pad configured to contact the underside of the patient's lower jaw in the area of the anterior triangle behind the mandibular symphysis and to be received in a small hollow of the patient's jaw. In use, the pad can apply force against a surface of the patient's lower jaw in order to push it forwardly and upwardly. The pad preferably is secured to a movable post that can be positioned such that a desired amount of force is applied to the patient's lower jaw.

11 Claims, 1 Drawing Sheet

Related U.S. Application Data

(60) Provisional application No. 61/528,115, filed on Aug. 26, 2011.

(58) Field of Classification Search
CPC ............... A61F 13/12; A61F 13/128; A61F 2002/3623; A61F 2002/365; A61M 16/00
See application file for complete search history.

(56) References Cited

U.S. PATENT DOCUMENTS

| | | | |
|---|---|---|---|
| 5,092,346 A | 3/1992 | Hays et al. | |
| 5,361,416 A * | 11/1994 | Petrie | A42B 3/08 |
| | | | 2/171 |
| 5,365,945 A | 11/1994 | Halstrom | |
| 5,427,117 A | 6/1995 | Thornton | |
| 5,462,066 A | 10/1995 | Snyder | |
| 5,566,683 A | 10/1996 | Thornton | |
| 5,570,704 A | 11/1996 | Buzzard et al. | |
| 5,687,743 A * | 11/1997 | Goodwin | A61F 5/56 |
| | | | 128/848 |
| 5,794,627 A | 8/1998 | Frantz et al. | |
| 5,810,013 A | 9/1998 | Belfer | |
| 5,921,241 A | 7/1999 | Belfer | |
| 6,129,084 A | 10/2000 | Bergersen | |
| 6,918,394 B2 * | 7/2005 | Matsuda | A61F 5/56 |
| | | | 128/848 |
| 6,981,503 B1 | 1/2006 | Shapiro | |
| 7,174,895 B2 | 2/2007 | Thornton et al. | |
| 7,178,525 B2 | 2/2007 | Matula et al. | |
| 7,225,811 B2 | 5/2007 | Ruiz et al. | |
| 8,770,196 B2 * | 7/2014 | Peake | A61M 16/00 |
| | | | 128/207.11 |
| 2006/0005840 A1 * | 1/2006 | Cannon | A61M 16/0683 |
| | | | 128/207.11 |
| 2007/0209663 A1 * | 9/2007 | Marque | A61M 16/0683 |
| | | | 128/207.11 |

OTHER PUBLICATIONS

Carex Health Brands, Boston, Massachusetts, item No. FGP73000 0000, http://www.carex.com/item/FGP73000+0000/Cervical-Collar/#.WsZFZ7g6rke.

* cited by examiner

AMELIORATION OF SLEEP APNEA AND OTHER OBSTRUCTIVE BREATHING DISORDERS

REFERENCE TO PRIOR APPLICATIONS AND PATENTS

The present application claims priority from all of the following applications and/or patents, wherein the present application is a continuation-in-part of application Ser. No. 14/471,849, filed Aug. 28, 2014 by Anthony J. DeRiso II and Albert N. Santilli, entitled Sleep Apnea Prevention, now U.S. Pat. No. 10,098,780, which is a continuation-in-part of application Ser. No. 13/594,625, filed Aug. 24, 2012 by Anthony J. DeRiso II and Albert N. Santilli, entitled Sleep Apnea Prevention, now U.S. Pat. No. 9,775,739 B2, issued Oct. 3, 2017, which claimed priority from provisional application Ser. No. 61/528,115, filed Aug. 26, 2011 by Anthony J. DeRiso II and Albert N. Santilli, entitled Sleep Apnea Prevention. The disclosures of all of the noted applications and/or patents are incorporated herein by reference for all purposes.

BACKGROUND OF THE INVENTION

1. Field of the Invention

The present invention relates to the field of ameliorating snoring and sleep apnea, specifically, obstructive sleep apnea (OSA), as well as other obstructive breathing disorders such as those that may occur during post-surgery induced sleep.

2. Description of the Prior Art

Snoring and sleep apnea are common sleep disorders caused by muscle relaxation and a narrowed pharynx. During sleep, the lower jaw muscles relax and in response the soft palate, uvula, and tongue relax and move to the back of the oral cavity. Consequently, the pharynx narrows. The air passing through a narrowed pharynx may cause the throat to vibrate which causes snoring.

In some people, the pharynx closes so much that enough air can't get through to the lungs. When this happens, the brain sends an alarm to open the airway. Most often, this is associated with a brief arousal from sleep. The brain quickly re-activates the muscles that hold the throat open, air passes through again, and the brain goes back to sleep. The repetitive episodes of complete or partial blockage of breathing are characteristic of obstructive sleep apnea (OSA). According to the American Sleep Apnea Association, more than 12 million Americans suffer from sleep apnea and it is estimated that 10 million remain undiagnosed. If sleep apnea is untreated, it can cause high blood pressure, weight gain, cardiovascular disease, and memory problems to name a few.

There are a variety of treatments to prevent sleep apnea and snoring. Drugs such as muscle relaxants have been used in an attempt to prevent closure of the pharynx during sleep. Masks of various sorts have been used in an attempt to provide gas under positive pressure to the pharynx so that breathing can be maintained. Numerous mechanical approaches also have been attempted. Typically, these involve some sort of dental appliance that is inserted into the mouth and that moves the lower jaw forward relative to the maxilla. By repositioning the lower jaw in a forward position, it is believed that the breathing passage will be kept open during sleep, thereby preventing both snoring and sleep apnea.

Mandibular advancement devices, dental appliances or oral mandibular advancement devices attempt to prevent the tongue from blocking the throat and/or anteriorly advance the lower jaw forward and help keep the airway open during sleep. Other types of treatments range from behavior and lifestyle changes, mechanical therapy, or surgery.

There are several problems with the foregoing approaches. Generally, the use of drugs is undesirable for a number of reasons, including possible dependence on such drugs. Masks with hoses are not well-tolerated and providing a source of pressurized gas can be complex and expensive. With respect to mechanical devices, often it is necessary for a custom-fit appliance to be used, which increases the cost to the patient. Prolonged use of such an appliance also has been reported to permanently change the bite characteristics of the patient.

As used herein, the words "patient" and "user" are used interchangeably. Use of the word "patient" is not intended to suggest that the invention is suitable only for use in a clinical or medical environment, or that it should be used only under the guidance of a medical professional. It is expected that the invention will be amenable to over the counter sales on a non-prescription basis. Further, terms such as "upper," "vertical," and other, similar terms are used herein to describe the position and/or relationship of certain components of the invention as a matter of convenience of description. The use of such terms is not intended to limit the invention since the invention can be used in a number of orientations.

SUMMARY OF THE INVENTION

The present invention provides a method and apparatus for ameliorating sleep apnea and other obstructive breathing disorders that addresses the foregoing concerns. The apparatus includes a collar in the nature of a cervical collar. The collar is configured to encircle the user's neck and preferably be held in place by hook and loop fasteners. The underside of the collar rests upon the user's clavical bones/superior portion of the trapezius muscle, while the upper side of the collar engages the underside of the user's throat, lower jaw and base of the skull.

The collar includes a jaw-engagement mechanism disposed at the front, central portion of the collar. The jaw-engagement mechanism includes a pad that preferably is vertically adjustable. The pad is configured to contact the underside of the user's lower jaw in the area of the anterior triangle behind the mandibular symphysis and to be received in a small hollow of the user's jaw. By appropriate adjustment of the pad, the pad will apply force against a surface of the user's lower jaw in order to push it forwardly and upwardly using relatively small forces. In this manner, the apparatus will prevent the tongue from blocking the throat and/or advance the lower jaw forward and help keep the airway open.

One of the advantages of the invention is that nothing is disposed within the user's mouth. Accordingly, nothing contacts the user's teeth and there is little or no chance that the bite characteristics of the user will change with prolonged use. Although the collar and pad need to be adjusted to fit each individual user, such adjustment should be easy to accomplish by the user. Another advantage is that the user's mouth is kept closed, thereby requiring breathing through the nose and lessening the chance that snoring will occur. Moreover, the invention is inexpensive to manufacture and avoids the use of an uncomfortable mask or other device that would be in contact with the user's face or head. It is believed that the collar will be well tolerated by most users and will be unlikely to disturb or interrupt normal sleeping positions.

Another advantage of the invention is that it can be used to ameliorate breathing disorders other than sleep apnea. For example, it may be necessary to induce sleep in a patient after a surgical procedure and to reduce the chances that the patient's breathing will be obstructed. Due to the simplicity and ease of use of the device, medical personnel will be able to apply the device to a sleeping patient and adjust it as necessary. Similar uses could occur in an emergency room when a traumatized or injured patient may need assistance in keeping the airway open.

DESCRIPTION OF THE PREFERRED EMBODIMENT

Figure 1:
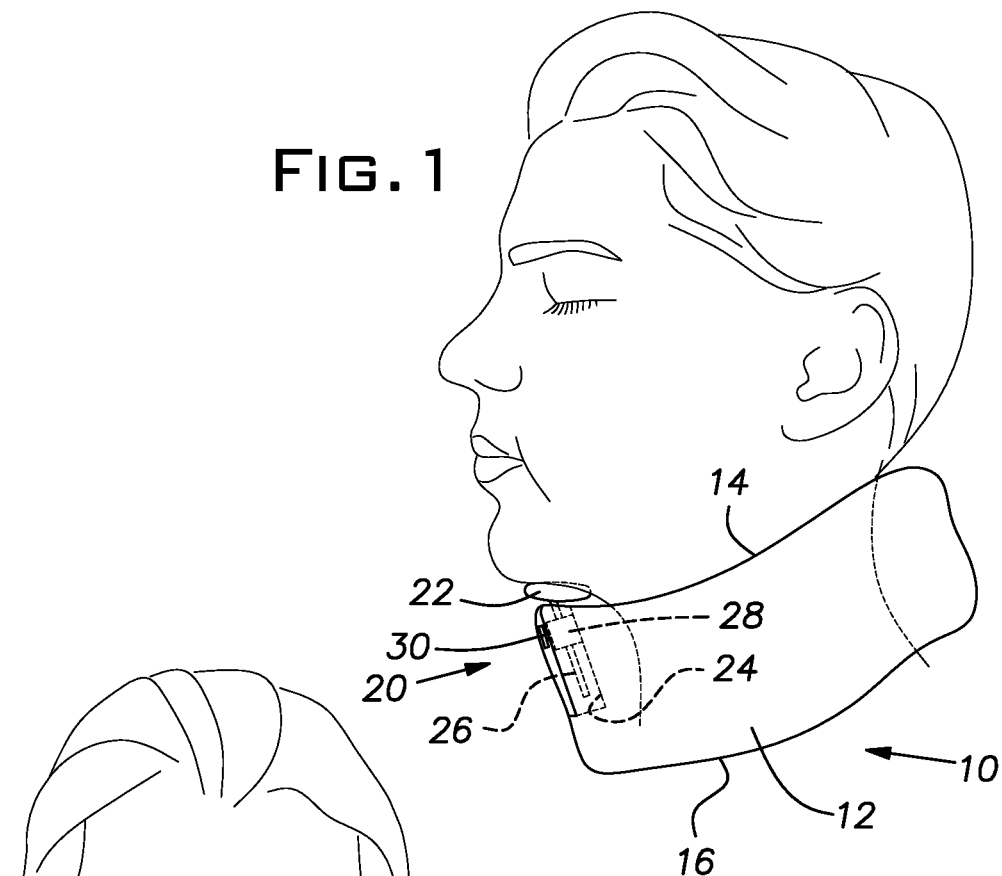
FIG. 1 is a side elevation view of a collar according to the present invention, with a pad engaging a portion of a patient's lower jaw.
Figure 2:
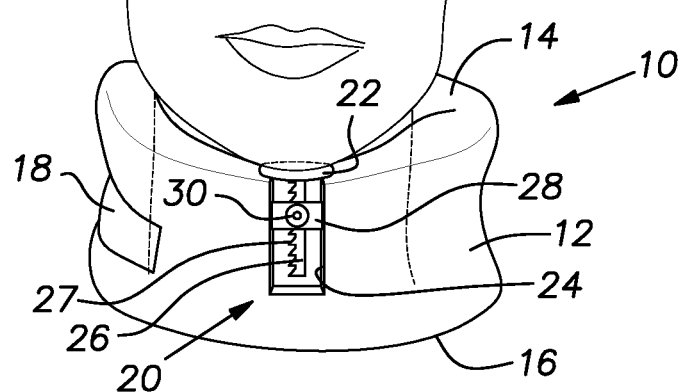
FIG. 2 is a front elevation view of the collar of FIG. 1.

Referring to FIG. 1, a collar 10 according to the current invention is shown. The collar 10 is in the nature of a cervical collar and comprises a padded portion 12 that can be wrapped around a patient's neck and held in place by a hook and loop fastener 18. Padded portion 12 has an upper surface 14 and a lower surface 16. The lower surface 16 rests upon the user's clavical bones/superior portion of the trapezius muscle, while the upper surface 14 engages the underside of the user's throat, lower jaw and base of the skull.

The collar 10 further comprises a jaw-engagement mechanism 20 that is located in the front portion of padded portion 12. The jaw-engagement mechanism 20 includes a small pad 22. A housing 24 is disposed within an opening formed at the front of the collar 10. The pad 22 is mounted to the upper end of a post 26 which is disposed within the housing 24 for vertical movement therein. The post 26 includes a plurality of notches or teeth 27 along one side. A crossbar 28 is disposed across the front of the housing 24, and carries a spring-biased, movable pin 30. The pin 30 is engageable with the notches 27 on the side of the post 26. The engagement between the notches 27 and the pin 30 is in the nature of a ratchet and pawl mechanism. The pin 30 is spring-biased to a notch-engaging position, but it can be moved against spring bias to a notch-disengaging position.

The collar 10 can be of any construction so long as it can be configured as described herein. It is expected that known cervical collars will be able to be modified to accomplish the purposes of the present invention. A cervical collar that can be modified for use as part of the invention is commercially available from ITA-MED Co., 25377 Huntwood Avenue, Hayward, Calif. 94544, model no. CC-260. A disclosure of the cervical collar in question, which disclosure is incorporated by reference herein, can be found at http://www.ita-med.com/our-products/back-neck-supports/cervical-collars/ita-med-rigid-plastic-cervical-collar-i-cc-260.html. This cervical collar is a rigid plastic cervical collar trimmed with foam padding and washable vinyl. It has a hook-and-loop closure and vent openings to increase comfort. The collar in question is height-adjustable from 3.5 inches to 4.5 inches and is available in different sizes.

Another suitable commercially available cervical collar is made by Carex Health Brands, Boston, Mass., item no. FGP73000 0000. A disclosure of the cervical collar in question, which disclosure is incorporated by reference herein, can be found at http://www.carex.com/item/FGP73000+0000/Cervical-Collar/#.WsZFZ7g6rke.

It is expected that most or all of the components of the present invention can be made of inexpensive materials such as foam, plastic, rubber, or similar materials. The use of such materials is expected to greatly decrease the cost of the device such that cost will not be a factor in a patient's acquisition of the device. Further, because the device is adjustable by the patient (or by a third party in the case of post-surgery induced sleep or emergency room use), it is expected that there will be no need to have custom-fit components. The avoidance of the use of custom-fit components is expected to reduce the cost of the device.

As indicated previously, the collar 10 can include vent openings. Such vent openings can be of any number or configuration so long as the collar 10 has adequate structural strength. For example, the vent openings can be circular or in the form of circumferentially extending windows. The use of such vent openings is intended to provide aeration so that the user will perspire less and be more comfortable. It is expected that increased comfort will encourage the user to wear the device for whatever time is necessary to produce a favorable result.

In use, the collar 10 is wrapped around the user's neck and secured in place by the hook and loop fastener 18. The jaw-engagement mechanism 20 is adjusted by extending the post 26 so that the pad 22 makes contact with the patient's lower jaw in the area of the anterior triangle, behind the mandibular symphysis. The configuration of the lower jaw in this region is in the nature of a small "hollow" that will receive the pad 22 and which will provide a surface against which force can be applied. Preferably, the pad 22 is rounded on that portion that contacts the lower jaw. The post 26 can be extended to different positions in order to vary the force applied to the patient's jaw by the pad 22. The positions that the post 26 can be extended can vary from one where the pad 22 is approximately even with the upper surface 14, to a position where the pad 22 is extended one or more inches.

The interaction between the notches 27 and the pin 30 will maintain the pad 22 in a desired extended position, i.e., the notches 27 and the pin 30 will prevent retraction of the pad 22 until the user disengages the pin 30 from the notches 27. After the pin 30 is disengaged from the notches 27, the post 26, with pad 22 attached, can be retracted into the housing 24.

Although the present invention has been described in detail, it will be apparent to those skilled in the art that various changes and modifications can be made without departing from the true spirit and scope of the invention as hereinafter claimed. For example, any other known technique for adjusting the position of relatively movable parts can be used to support the pad 22 and adjust its position. Such other techniques include, without limitation, openings in the post along its length into which the pin 30 can fit, an adjustable friction fit between the housing 24 and the post 26, a threaded member projecting forwardly of the post 26 that can receive a nut for tightening against a portion of the housing 24 having a vertical slot, etc. It is intended that all such changes and modifications be encompassed within the scope of the present disclosure and claims.

What is claimed is:

1. A device for ameliorating sleep apnea and other obstructive breathing disorders in a patient having a neck, a lower jaw having an underside, a mandibular symphysis, an anterior triangle behind the mandibular symphysis, and a small hollow, comprising:

a collar configured to encircle the patient's neck, the collar having a front disposed beneath the patient's lower jaw; and a jaw-engagement mechanism carried by the collar, the jaw-engagement mechanism including a pad configured to contact the underside of the patient's lower jaw in the area of the anterior triangle behind the mandibular symphysis and to be received in a small hollow of the patient's jaw, a vertically oriented housing disposed at the front of the collar; a vertically movable post disposed within the housing, the post having an upper end to which the pad is secured and a plurality of notches disposed along a portion of the length of the post, the post being movable such that the pad can be located and secured in a desired position relative to the patient's lower jaw, and a pin connected to and carried by the housing, the pin being engageable with the notches, whereby the pad can apply force against a surface of the patient's lower jaw in order to push it forwardly and upwardly.

2. The device of claim 1, further comprising a hook and loop fastener, the hook and loop fastener configured to secure the collar in place about the patient's neck.

3. The device of claim 1, further comprising;
an opening formed in the front of the collar; and
the housing being disposed within the opening.

4. The device of claim 1, wherein the pin is movable between notch-engaging and notch-disengaging positions.

5. The device of claim 1, wherein the pin is spring-biased into engagement with the notches.

6. The device of claim 1, wherein the pad is rounded.

7. The device of claim 1, further comprising one or more vent openings included as part of the collar.

8. A device for ameliorating sleep apnea and other obstructive breathing disorders in a patient having a neck, a lower jaw having an underside, a mandibular symphysis, an anterior triangle behind the mandibular symphysis, and a small hollow, comprising:

a collar configured to encircle the patient's neck, the collar including a front disposable beneath the patient's lower jaw and a hook and loop fastener, the hook and loop fastener configured to secure the collar in place about the patient's neck;

a jaw-engagement mechanism carried by the collar, the jaw-engagement mechanism including:
an opening formed in the front of the collar;
a vertically oriented housing disposed within the opening;
a vertically movable post disposed within the housing, the post having an upper end and notches along at least a portion of its length;
a pad secured to the upper end of the post, the pad having a jaw-engaging surface, the jaw-engaging surface being rounded; and a pin connected to and carried by the housing, the pin being engageable with the notches and movable between notch-engaging and notch-disengaging positions, the pin being spring-biased into engagement with the notches; and whereby the pad can be positioned relative to a patient's lower jaw so as to apply force against a surface of the patient's lower jaw in order to push it forwardly and upwardly.

9. A method for ameliorating sleep apnea and other obstructive breathing disorders in a patient having a neck, a lower jaw having an underside, a mandibular symphysis, an anterior triangle behind the mandibular symphysis, and a small hollow, comprising:

providing a collar configured to encircle the patient's neck, the collar including a jaw-engagement mechanism having a pad configured to contact the underside of the patient's lower jaw in the area of the anterior triangle behind the mandibular symphysis and to be received in a small hollow of the patient's lower jaw;

providing a vertically oriented opening in a front of the collar;

providing a housing;

disposing the housing within the opening;

providing a post, the post having an upper end and notches along at least a portion of its length;

disposing the post within the housing such that the post is vertically movable within the housing;

securing the pad to the upper end of the post;

providing a pin connected to and carried by the housing, the pin being engageable with the notches and movable between notch-engaging and notch-disengaging positions, the pin being spring-biased into engagement with the notches;

disposing the collar about the patient's neck with the pad in contact with the underside of the patient's lower jaw in the area of the anterior triangle behind the mandibular symphysis with the pad being received in a small hollow of the patient's jaw;

moving the post, and thereby the pad, to a desired position relative to the patient's lower jaw;

applying force through the pad against a surface of the patient's lower jaw in order to push it forwardly and upwardly; and engaging the notches and the pin such that the pad is maintained in a desired position relative to the patient's lower jaw.

10. The method of claim 9, further comprising the steps of:

providing a hook and loop fastener for the collar; and
securing the collar in place around the patient's neck by tightening the hook and loop fastener.

11. The method of claim 9, further comprising the step of providing one or more vent openings as part of the collar.

* * * * *